United States Patent
Zhao et al.

(10) Patent No.: US 10,973,468 B2
(45) Date of Patent: Apr. 13, 2021

(54) DEEP LEARNING APPROACH FOR LONG TERM, CUFFLESS, AND CONTINUOUS ARTERIAL BLOOD PRESSURE ESTIMATION

(71) Applicant: The Chinese University of Hong Kong, Hong Kong (CN)

(72) Inventors: Ni Zhao, Guangdong (CN); Peng Su, Hubei (CN); Yuanting Zhang, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 216 days.

(21) Appl. No.: 16/033,744

(22) Filed: Jul. 12, 2018

(65) Prior Publication Data

US 2020/0015755 A1    Jan. 16, 2020

(51) Int. Cl.
*A61B 5/00* (2006.01)
*A61B 5/0205* (2006.01)
(Continued)

(52) U.S. Cl.
CPC .......... *A61B 5/7267* (2013.01); *A61B 5/0205* (2013.01); *A61B 5/316* (2021.01);
(Continued)

(58) Field of Classification Search
CPC ... A61B 5/7267; A61B 5/7278; A61B 5/7203; A61B 5/0402; A61B 5/04017; A61B 5/0205; A61B 5/0245; A61B 5/02108; A61B 5/02416; G16H 50/20; G16H 40/63; G06N 3/0445; G06N 3/04; G06N 3/0454

See application file for complete search history.

(56) References Cited

U.S. PATENT DOCUMENTS 5,680,866 A    10/1997    Kangas et al.
2011/0004069 A1*    1/2011    Ochs ................ A61B 5/02416
                                                        600/300

(Continued)

OTHER PUBLICATIONS

End-To-End Deep Learning Architecture for Continuous Blood Pressure Estimation Using Attention Mechanism Heesang Eom, Dongseok Lee, Seungwoo Han, Yuli Sun Hariyani, Yonggyu Lim, Illsoo Sohn, Kwangsuk Park, Cheolsoo Park Sensors (Basel) Apr. 2020; 20(8): 2338. Published online Apr. 20, 2020. (Year: 2020).*

(Continued)

*Primary Examiner* — Amanda K Hulbert
*Assistant Examiner* — Natasha Patel
(74) *Attorney, Agent, or Firm* — Saliwanchik, Lloyd & Eisenschenk

(57) ABSTRACT

Methods and devices for long term, cuffless, and continuous arterial blood pressure estimation using an end-to-end deep learning approach are provided. A deep learning system comprises three modules: a deep convolutional neural network (CNN) module for learning powerful features; a one- or multi-layer recurrent neural network (RNN) module for modeling the temporal dependencies in blood pressure dynamics; and a mixture density network (MDN) module for predicting final blood pressure value. This system takes raw physiological signals, such as photoplethysmogram and/or electrocardiography signals, as inputs and yields arterial blood pressure readings in real time.

20 Claims, 3 Drawing Sheets

(51) Int. Cl.
*G16H 50/20* (2018.01)
*A61B 5/316* (2021.01)
*A61B 5/318* (2021.01)
*G06N 3/04* (2006.01)
*A61B 5/024* (2006.01)
*A61B 5/021* (2006.01)
*A61B 5/0245* (2006.01)

(52) U.S. Cl.
CPC ............ *A61B 5/318* (2021.01); *A61B 5/7203* (2013.01); *A61B 5/7278* (2013.01); *G16H 50/20* (2018.01); *A61B 5/0245* (2013.01); *A61B 5/02108* (2013.01); *A61B 5/02416* (2013.01); *G06N 3/04* (2013.01); *G06N 3/0445* (2013.01); *G06N 3/0454* (2013.01)

(56) References Cited

U.S. PATENT DOCUMENTS

| | | | | |
|---|---|---|---|---|
| 2012/0022336 | A1* | 1/2012 | Teixeira | A61B 5/0205 600/300 |
| 2015/0230750 | A1* | 8/2015 | McDarby | A61B 5/0816 600/407 |
| 2016/0210435 | A1* | 7/2016 | Neumann | G09B 23/288 |
| 2019/0209022 | A1* | 7/2019 | Sobol | A61B 5/1112 |

OTHER PUBLICATIONS

Lipton, Z. C. et al., "Learning to Diagnose with LSTM Recurrent Neural Networks," *ICLR*, 2016, pp. 1-18.

Sideris, C. et al., "Building Continuous Arterial Blood Pressure Prediction Models Using Recurrent Networks," *Smart Computing (SMARTCOMP)*, IEEE International Conference on IEEE, 2016, pp. 1-5.

Su, P. et al., "Long-term Blood Pressure Prediction with Deep Recurrent Neural Networks," *IEEE*, 2018, pp. 1-7, IEEE Conference on Biomedical and Health Informatics, 2018, pp. 1-7.

Ding, X.R. et al., "Coherence Analysis of Invasive Blood Pressure and Its Noninvasive Indicators for Improvement of Cuffless Measurement Accuracy", Engineering in Medicine and Biology Society (EMBC), 2017 39th Annual International Conference of the IEEE, 2255-2258.

Su, P. et al., "Predicting Blood Pressure with Deep Bidirectional LSTM Network", arXiv:1705.04524v1 [cs.LG], May 12, 2017, pp. 1-19.

Ruiz-Rodríguez, J.C. et al., "Innovative continuous non-invasive cuffless blood pressure monitoring based on photoplethysmography technology", Intensive Care Medicine, 2013, 39:1618-1625, Springer-Verlag Berlin Heidelberg and ESICM 2013.

Nomura Investment Forum 2011, Omron's Strengths—Medium and Long Term Strategy of Main Businesses—, OMRON Corporation, Nov. 29, 2011, 25 pages.

Zheng, Y.L. et al., "Unobtrusive Sensing and Wearable Devices for Health Informatics", IEEE Transactions on Biomedical Engineering, 61(5):1538-1554, May 2014.

Luo, N. et al., "Flexible Piezoresistive Sensor Patch Enabling Ultralow Power Cuffless Blood Pressure Measurement", Advanced Functional Materials, 2016, 26:1178-1187, 2015 Wiley-VCH Verlag GmbH & Co. KGaA, Weinheim.

* cited by examiner

DEEP LEARNING APPROACH FOR LONG TERM, CUFFLESS, AND CONTINUOUS ARTERIAL BLOOD PRESSURE ESTIMATION

BACKGROUND OF THE INVENTION

As the leading risk factor of cardiovascular diseases (CVD), high blood pressure (BP) is commonly used as the critical criterion for diagnosing and preventing CVD. Therefore, accurate and continuous BP monitoring is imperative for early detection and intervention of CVD. Traditional cuff-based BP measurement devices are bulky, uncomfortable, and may only provide snapshot measurements. These disadvantages hinder nighttime monitoring and precise diagnosis of different CVD symptoms.

BRIEF SUMMARY OF THE INVENTION

Embodiments of the subject invention provide cuffless electronic devices for arterial blood pressure (BP) estimation/prediction that rely on an algorithm to extract arterial BP from multiple sequential physiological signals, as well as methods of using and manufacturing the same.

The deep learning approach described herein can automatically extract key features that are needed for accurate BP prediction, regardless of input signal quality. In other words, the approach can be trained to discard irrelevant information and retain important clues for BP prediction. Instead of yielding BP prediction via linear projection at the last stage, the mixture density network (MDN) models the BP as a mixture of Gaussian distributions, allowing for a larger generalization capability. This deep learning approach outperforms the current BP extraction methods in terms of robustness in signal processing, long-term reliability, accuracy generality, and cost.

DETAILED DISCLOSURE OF THE INVENTION

The following disclosure and exemplary embodiments are presented to enable one of ordinary skill in the art to make and use a cuffless electronic device for arterial blood pressure (BP) estimation/prediction, according to embodiments of the subject invention. Various modifications to the embodiments will be readily apparent to those skilled in the art and the generic principles herein may be applied to other embodiments. Thus, the devices and methods related to the cuffless electronic device are not intended to be limited to the embodiments shown, but are to be accorded the widest scope consistent with the principles and features described herein.

Embodiments of the subject invention provide devices for continuous arterial blood pressure estimation using an end-to-end deep learning approach. A device can comprise three modules: a deep convolutional neural network (CNN) module for learning powerful features; a one- or multi-layer recurrent neural network (RNN) module to model the temporal dependencies in blood pressure dynamics; and a mixture density network (MDN) module to predict final blood pressure value. These three modules construct an end-to-end trainable deep learning model. The herein described systems can accept raw physiological signals (e.g. photoplethysmogram (PPG), electrocardiography (ECG or EKG), etc.) as inputs and after calculation yield arterial blood pressure readings in real time.

Figure 1:
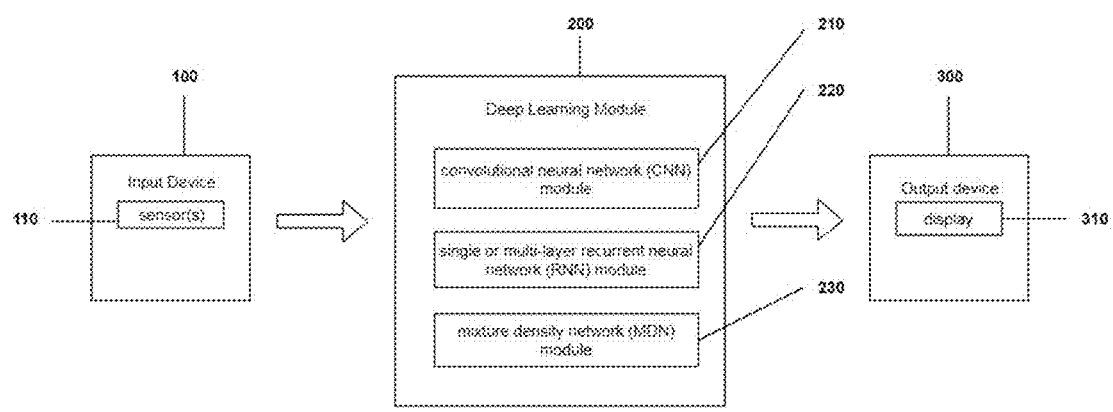
FIG. 1 is a block diagram illustrating the arterial blood pressure (BP) estimation/prediction system.

FIG. 1 is a block diagram illustrating an arterial blood pressure (BP) estimation/prediction system according to an embodiment of the subject invention. The arterial blood pressure (BP) estimation/prediction system includes an input device 100, a deep learning module 200, and an output device 300. The input device comprises a sensor 110 or a plurality of sensors 110 including ECG, EKG, or PPG sensors. The deep leaning module 200 comprises a convolutional neural network (CNN) module 210, a one- or multi-layer recurrent neural network (RNN) module 220, and a mixture density network (MDN) module 230.

Raw physiological signals from a patient can be sensed by the input device 100. The input device 100 can transmit the physiological signals to the deep learning module 200. The CNN module 210 can extract features from the physiological signals. The RNN module 220 comprising Long-Short Term Memory Networks (LSTMs) can model the temporal dependencies in blood pressure dynamics. The MDN module 230 can to output the arterial blood pressure estimation to an output device 300.

A CNN module 210 comprises a plurality of convolutional and subsampling layers. Each convolutional layer can have a plurality of filters. The size of the filters influences the locally connected structure. The filters can each be convolved with the physiological signals to produce a plurality of feature maps. Each feature map can be subsampled, down-sampled, and up-sampled, for example by mean/average or max pooling, over a plurality of contiguous regions. An additive bias and a nonlinear activation function can be applied to each feature map.

Figure 2:
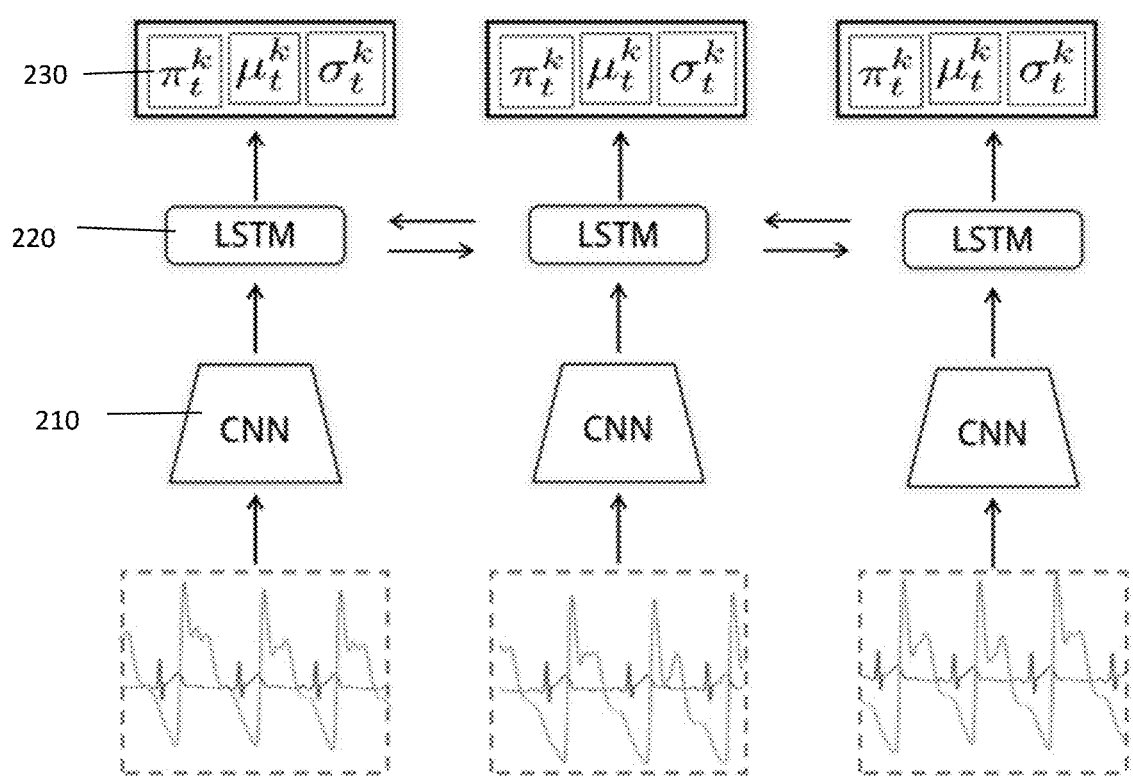
FIG. 2 is a diagram illustrating an example of the described method for cuffless BP estimation.

FIG. 2 is a diagram illustrating an example of the described method for cuffless BP estimation. The CNN module 210 can directly take raw physiological signals, i.e., ECG, EKG, and PPG, as input. The CNN module 210 can generate dense feature maps that capture patterns in the input data. These informative feature maps can be fed into the RNN module 220 comprising a bidirectional (LSTM) to process the blood pressure dynamics. The mixture density network module 230 can take its inputs from the hidden state of the last LSTM layer and compute a mixture of Gaussian distribution.

Figure 3:
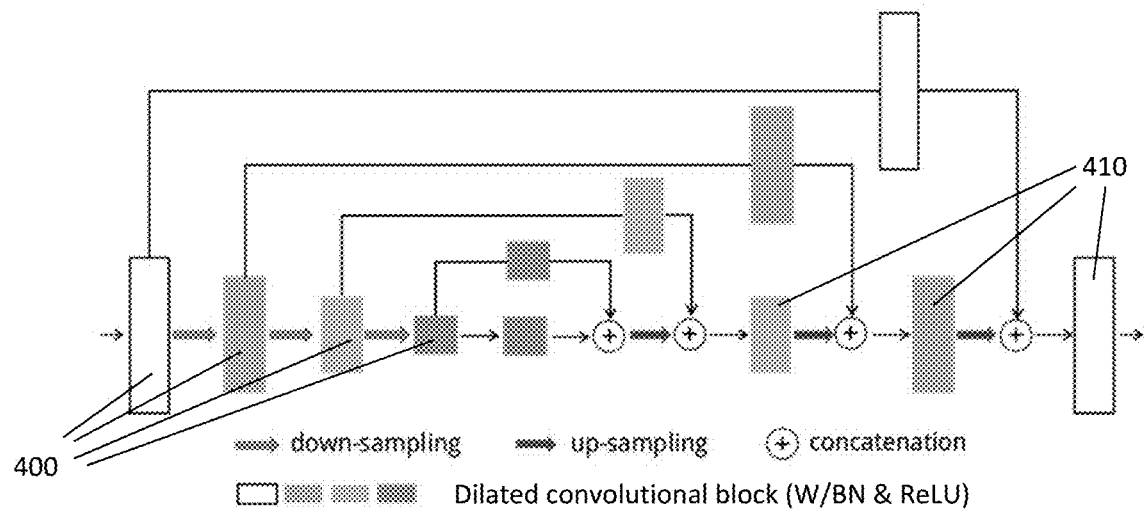
FIG. 3 is a diagram illustrating an example of the convolutional neural network module.

FIG. 3 illustrates an example of the CNN module. Features can be processed across different scales and consolidated to best capture the various patterns of multiple time resolutions.

In one embodiment, each convolutional block 400 comprises two convolutional layers and a rectified linear unit (ReLU). In certain embodiments down-sampling is performed by a pooling layer, including a max pooling or average pooling, to reduce the number of parameters and computation in the module. Each upsampling block 410 comprises a deconvolutional layer and a ReLU. In certain embodiments, batch normalization (BN) can be employed to normalize the output of certain layers. The output of certain layers can be concatenated and an output can be generated.

The physiological signals sensed from the patient can be filtered to remove noise and redundant information prior to being transmitted to the CNN module. The CNN can be a one dimensional (1D) CNN, a two dimensional (2D) CNN, or a three dimensional (3D) CNN. The convolution operation in the CNN can be a generic convolution or a dilated convolution.

In one embodiment, the CNN module 210 can be configured to be a cascade multi-layer structure or cascade multi-layer structure incorporated with skip connections. The skip connections can merge lower layer feature maps with higher layer feature maps to capture different time-scale variation patterns.

In another embodiment, the CNN module 210 can be configured to operate on different time-scales of input data. For example, a feature pyramid can be constructed by the CNN module 210 and different scale features can be merged for downstream machine learning tasks.

Figure 4:
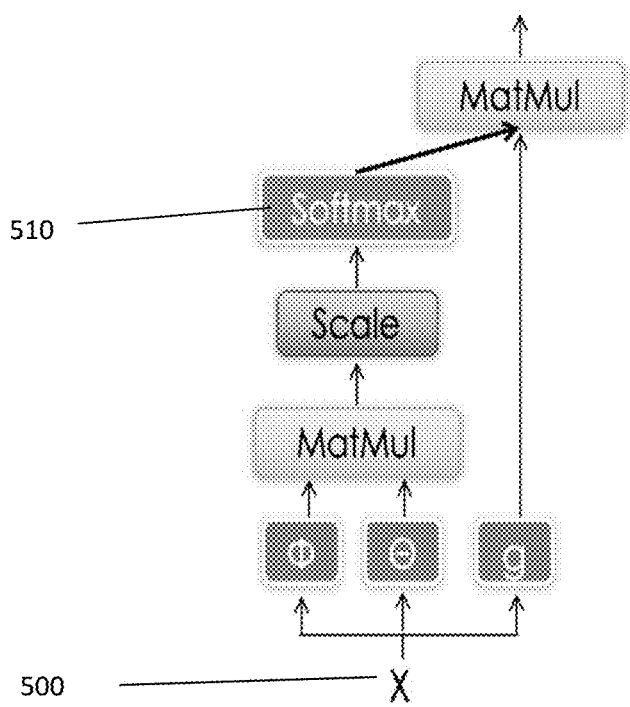
FIG. 4 is a diagram illustrating an example of an attention mechanism.

In one embodiment, the CNN module 210 is configured to incorporate an attention mechanism and/or an algorithm for position embedding of inputs. In this embodiment the deep learning module 200 operates without the RNN module 220. The attention mechanism can direct the CNN module 210 to focus on certain elements of the physiological signals. In one embodiment, an attention mechanism module can utilize a scaled dot-product attention approach (see, for example, FIG. 4). The input X can be re-weighted through the use of an attention mask and the re-weighted output can be normalized using a Softmax function. After input X has been refined by the attention mechanism module, the output of the attention mechanism module can be fed into a next module of the process. The product of $\phi(x)$ and $\theta(x)$ can be normalized by the input dimension $d_\theta(x)$ as follows:

$$\text{Attention}(\phi(x), \theta(x), g(x)) = \text{softmax}\left(\frac{\phi(x)\theta(x)^T}{\sqrt{d_\theta(x)}}\right)g(x), \quad (1)$$

wherein $\phi$, $\theta$, and g are each respective functions of x. In this embodiment, the CNN module 210 has the capability of modeling temporal deficiencies, which can replace the role of the RNN module 220. In another embodiment, the attention mechanism can enhance CNN feature maps with attention masks. The attention masks can be generated from corresponding feature maps by various attention mechanism algorithms.

The RNN module 220 can comprise a one- or multi-layer RNN. The RNN can be configured to be a standard RNN, a gated recurrent unit (GRU), a LSTM network, or other variant. The RNN module 220 can comprise a standard RNN or a bidirectional RNN. In certain embodiments, the RNN module 220 can be incorporated with an attention mechanism for improving prediction accuracy.

The LSTM network can comprises different memory blocks or cells in sequence. Two states, the cell state and the hidden state, can be transferred to a subsequent cell. Each memory block or cell can store memory and each block can be reconfigured through different gates: input gates, output gates, and forget gates.

An MDN module 230 can comprise a flexible framework for modeling an arbitrary conditional probability distribution as a mixture of distributions, parameterized by functions of the physiological signals. An MDN module 230 can be configured to parameterize a mixture model comprising certain predefined types of distributions.

In one embodiment, the MDN module 230 can model the blood pressure prediction as a classification problem. The outputs can then become a mixture of Gaussian distributions, which is a general case of mean square minimization (MSE). If, however, the output has only one Gaussian distribution, the MDN module 230 function will degrade to a MSE loss.

The cuffless electronic device can operate through an end-to-end framework and be trained by a backpropagation algorithm. The backpropagation algorithm can calculate the gradient of an error function with respect to the deep learning module's weights.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processer reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein (including those in the "References" section) are incorporated by reference in their entirety, including all figures and tables, to the extent they are not inconsistent with the explicit teachings of this specification.

What is claimed is:

1. A method for long-term, cuffless, and continuous arterial blood pressure estimation, the method comprising:
   extracting features from a physiological signal using a deep convolutional neural network (CNN);

modeling temporal dependencies in blood pressure dynamics using a recurrent neural network (RNN); and outputting an estimate of arterial blood pressure using a mixture density network (MDN).

2. The method of claim 1, wherein the physiological signal comprises a single physiological signal.

3. The method of claim 2, wherein the single physiological signal comprises a photoplethysmogram (PPG) signal.

4. The method of claim 1, wherein the physiological signal comprises multiple physiological signals.

5. The method of claim 4, wherein the multiple physiological signals comprise a PPG signal and an electrocardiography (ECG or EKG) signal.

6. The method of claim 1, wherein the physiological signal is filtered to remove noise and redundant information.

7. The method of claim 1, further comprising training the CNN, the RNN, and the MDN through a backpropagation algorithm.

8. A system for long-term, cuffless, and continuous arterial blood pressure estimation, the system comprising:
   a deep convolutional neural network (CNN) configured to extract features from a physiological signal;
   a recurrent neural network (RNN) configured to model temporal dependencies in blood pressure; and
   a mixture density network (MDN) configured to output an estimate of arterial blood pressure.

9. The system of claim 8, wherein the CNN comprises a multi-layered convolutional neural network.

10. The system of claim 8, wherein the CNN is a one-dimensional (1D) CNN, a two-dimensional (2D) CNN, or a three-dimensional (3D) CNN.

11. The system of claim 8, wherein the CNN is configured to use generic convolution or dilated convolution.

12. The system of claim 8, wherein the CNN is configured to be a cascade multi-layer structure incorporated with skip connections, and wherein the skip connection merge lower layer feature maps with higher layer feature maps to capture different time-scale variation patterns.

13. The system of claim 8, wherein the CNN module is configured to work on a plurality of time-scales of input data.

14. The system of claim 8, wherein the RNN further comprises a one-layer recurrent neural network or a multi-layer recurrent neural network.

15. The system of claim 8, wherein the RNN comprises at least one of a standard RNN, a gated recurrent unit (GRU), and a long-short term memory (LSTM) network.

16. The system of claim 8, wherein the RNN comprises a standard RNN or a bidirectional RNN.

17. The system of claim 8, wherein the RNN comprises an attention mechanism.

18. The system of claim 8, wherein the MDN is configured to model a blood pressure prediction as a classification problem, and wherein an output comprises a mixture of Gaussian distribution.

19. A system for long-term, cuffless, and continuous arterial blood pressure estimation, the system comprising:
   a deep convolutional neural network (CNN) configured to extract features from a physiological signal and modeling temporal deficiencies, and comprising at least one of an attention mechanism and an algorithm configured to position-embed inputs; and
   a mixture density network (MDN) configured to output an estimate of arterial blood pressure.

20. The system of claim 19, wherein the attention mechanism enhances CNN feature maps with attention masks, and wherein the attention masks are generated from the feature maps.

* * * * *